US012589106B2

(12) United States Patent
Garcia-Rodenas et al.

(10) Patent No.: US 12,589,106 B2
(45) Date of Patent: \*Mar. 31, 2026

(54) NUTRITIONAL COMPOSITION COMPRISING A COMBINATION OF HUMAN MILK OLIGOSACCHARIDES TO IMPROVE THE GASTROINTESTINAL BARRIER

(71) Applicant: SOCIETE DES PRODUITS NESTLE S.A., Vevey (CH)

(72) Inventors: Clara Lucia Garcia-Rodenas, Forel (CH); Jane Mea M Natividad, Lausanne (CH); Andreas Rytz, Carrouge (CH)

(73) Assignee: Societe des Produits Nestle S.A., Vevey (CH)

( * ) Notice: Subject to any disclaimer, the term of this patent is extended or adjusted under 35 U.S.C. 154(b) by 914 days.

This patent is subject to a terminal disclaimer.

(21) Appl. No.: 17/416,573

(22) PCT Filed: Dec. 11, 2019

(86) PCT No.: PCT/EP2019/084604
§ 371 (c)(1),
(2) Date: Jun. 21, 2021

(87) PCT Pub. No.: WO2020/126734
PCT Pub. Date: Jun. 25, 2020

(65) Prior Publication Data
US 2022/0062311 A1     Mar. 3, 2022

(30) Foreign Application Priority Data
Dec. 21, 2018     (EP) ..................................... 18215208

(51) Int. Cl.
| | |
|---|---|
| A61K 31/702 | (2006.01) |
| A23L 33/00 | (2016.01) |
| A23L 33/125 | (2016.01) |
| A61K 31/07 | (2006.01) |
| A61K 31/122 | (2006.01) |
| A61K 31/14 | (2006.01) |
| A61K 31/197 | (2006.01) |
| A61K 31/202 | (2006.01) |
| A61K 31/355 | (2006.01) |
| A61K 31/375 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/519 | (2006.01) |
| A61K 31/525 | (2006.01) |
| A61K 31/593 | (2006.01) |

(Continued)

(52) U.S. Cl.
CPC .......... *A61K 31/702* (2013.01); *A23L 33/125* (2016.08); *A23L 33/40* (2016.08); *A61K 31/07* (2013.01); *A61K 31/122* (2013.01); *A61K*

*31/14* (2013.01); *A61K 31/197* (2013.01); *A61K 31/202* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61K 33/00* (2013.01); *A61K 33/04* (2013.01); *A61K 33/06* (2013.01); *A61K 33/18* (2013.01); *A61K 33/20* (2013.01); *A61K 33/26* (2013.01); *A61K 33/30* (2013.01); *A61K 33/32* (2013.01); *A61K 33/34* (2013.01); *A61K 33/42* (2013.01); *A61K 47/26* (2013.01); *A61P 1/00* (2018.01); *A61P 3/02* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 2007/0104700 A1 | 5/2007 | Garcia-Rodenas et al. | |
| 2009/0087540 A1* | 4/2009 | Haschke ................. | A23L 33/40 |
| | | | 426/601 |

(Continued)

FOREIGN PATENT DOCUMENTS

| | | |
|---|---|---|
| RU | 2473347 C1 | 1/2013 |
| WO | 2012092155 A1 | 7/2012 |

(Continued)

OTHER PUBLICATIONS

Silva, J. P., Navegantes-Lima, K. C., Oliveira, A. L., Rodrigues, D. V., Gaspar, S. L., Monteiro, V. V., . . . & Monteiro, M. C. (2018). Protective mechanisms of butyrate on inflammatory bowel disease. Current pharmaceutical design, 24(35), 4154-4166. (Year: 2018).*

(Continued)

*Primary Examiner* — Dale R Miller

(74) *Attorney, Agent, or Firm* — K&L Gates LLP

(57) ABSTRACT

The present invention relates to nutritional compositions comprising 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) for use in improving gastrointestinal barrier. In particular, the present invention relates to improving the gastrointestinal barrier in an infant, a young child or children aged above 3 years to 8 years.

11 Claims, 2 Drawing Sheets

(51) Int. Cl.

| | |
|---|---|
| *A61K 31/714* | (2006.01) |
| *A61K 33/00* | (2006.01) |
| *A61K 33/04* | (2006.01) |
| *A61K 33/06* | (2006.01) |
| *A61K 33/18* | (2006.01) |
| *A61K 33/20* | (2006.01) |
| *A61K 33/26* | (2006.01) |
| *A61K 33/30* | (2006.01) |
| *A61K 33/32* | (2006.01) |
| *A61K 33/34* | (2006.01) |
| *A61K 33/42* | (2006.01) |
| *A61K 47/26* | (2006.01) |
| *A61P 1/00* | (2006.01) |
| *A61P 3/02* | (2006.01) |

(56) References Cited

U.S. PATENT DOCUMENTS

| | | | |
|---|---|---|---|
| 2014/0294789 A1 | 10/2014 | David et al. | |
| 2014/0335065 A1 | 11/2014 | Davis et al. | |
| 2016/0310514 A1 | 10/2016 | Salomonsson et al. | |
| 2017/0258820 A1 | 9/2017 | Hennet et al. | |
| 2018/0064739 A1* | 3/2018 | Chichlowski | A23L 33/40 |
| 2018/0185398 A1* | 7/2018 | Vigsnæs | A61K 31/702 |
| 2020/0163981 A1* | 5/2020 | Rochat | A61K 9/0095 |

FOREIGN PATENT DOCUMENTS

| | | | | |
|---|---|---|---|---|
| WO | 2012092156 A1 | 7/2012 | | |
| WO | 2015071401 A1 | 5/2015 | | |
| WO | 2015071402 A1 | 5/2015 | | |
| WO | 2015071403 A1 | 5/2015 | | |
| WO | WO-2017103019 A1 * | 6/2017 | | A23L 33/135 |
| WO | 2017190754 A1 | 11/2017 | | |

OTHER PUBLICATIONS

Cacho, N. T., & Lawrence, R. M. (2017). Innate immunity and breast milk. Frontiers in immunology, 8, 584. (Year: 2017).*

Thurl, S., Munzert, M., Boehm, G., Matthews, C., & Stahl, B. (2017). Systematic review of the concentrations of oligosaccharides in human milk. Nutrition Reviews, 75(11), 920-933. (Year: 2017).*

Russian Office Action for Appl No. 2021120652/10 dated Nov. 10, 2023.

Lane et al. "Anti-infective bovine colostrum oligosaccharides: Campylobacter jejuni as a case study" International Journal of Food Microbiology, 2012, vol. 157, pp. 182-188.

Lin et al. "Necrotizing Enterocolitis: Recent Scientific Advances in Pathophysiology and Prevention" Seminars in Perinatology, 2008, vol. 32, pp. 70-82.

Kunz et al. "Bioactivity of Human Milk Oligosaccharides" Food Oligosaccharides: Production, Analysis and Bioactivity, Mar. 1, 2014, pp. 5-20, XP055274909.

Erney et al. "Variability of Human Milk Neutral Oligosaccharides in a Diverse Population" Journal of Pediatric Gastroenterology and Nutrition, 2000, vol. 30, pp. 181-192.

Priority Document of EP Application No. 18215208.2, filed on Dec. 21, 2018, 6 Pages.

Grtiz et al., "The Human Neonatal Gut Microbiome: A Brief Review", Pediatrics, vol. 03, 2015, pp. 1-12.

Arrieta et al., "The Intestinal Microbiome in Early Life: Health and Disease", Frontiers in Immunology, vol. 05, 2014, pp. 1-18.

Langerholc et al., "Novel and Established Intestinal Cell Line Models—An Indispensable Tool in Food Science and Nutrition", Trends in Food Science & Technology, vol. 22, 2011, Pages S11-S20.

Cencic et al., Functional Cell Models of the Gut and their Applications in Food Microbiology—A Review, International Journal of Food Microbiology, vol. 141, 2010, pp. S4-S14.

Natividad et al., "Blends of Human Milk Oligosaccharides Confer Intestinal Epithelial Barrier Protection in Vitro", Nutrients, vol. 12, 2020, pp. 1-13.

Hodges et al., "Infectious Diarrhea: Cellular and Molecular Mechanisms", Gut Microbes, vol. 01, Issue No. 01, 2010, pp. 4-21.

Rasmussen et al., "Human Milk Oligosaccharide Effects on Intestinal Function and Inflammation after Preterm Birth in Pigs", Journal of Nutritional Biochemistry, vol. 40, 2017, pp. 141-154.

Halpern et al., "The Role of Intestinal Epithelial Barrier Function in the Development of NEC", Tissue Barriers, vol. 03, Issue No. 1-2, 2015, pp. e1000707-1-e1000707-10.

Liu et al., "Butyrate: A Double-Edged Sword for Health?", Advances in Nutrition, vol. 09, 2018, pp. 21-29.

Holscher et al., "Human Milk Oligosaccharides Influence Intestinal Epithelial Cell Maturation In Vitro", Journal of Pediatric Gastroenterology and Nutrition, vol. 64, Issue No. 02, 2017, pp. 296-301.

Bych et al., "Production of Hmos using Microbial Hosts—From Cell Engineering to Large Scale Production", Current Opinion in Biotechnology, vol. 56, 2019, pp. 130-137.

Jacobi et al., "Nutritional Factors Influencing Intestinal Health of the Neonate", Advances in Nutrition, vol. 03, 2012, pp. 687-696.

Wang et al., "Butyrate Enhances Intestinal Epithelial Barrier Function via Up-Regulation of Tight Junction Protein Claudin-1 Transcription", Digestive Diseases and Science, vol. 57, 2012, pp. 3126-3135.

Canani et al., "Potential Beneficial Effects of Butyrate in Intestinal and Extraintestinal Diseases", World Journal of Gastroenterology, vol. 17, Issue No. 12, 2011, pp. 1519-1528.

Lozano et al., "Relationship between Oligosaccharides and Glycoconjugates Content in Human Milk and the Development of the Gut Barrier", Comprehensive Reviews in Food Science and Food Safety, vol. 18, 2019, pp. 121-139.

Xing et al., "Animal Models for Studying Epithelial Barriers in Neonatal Necrotizing Enterocolitis, Inflammatory Bowel Disease and Colorectal Cancer", Tissue Barriers, vol. 05, Issue No. 04, 2017, pp. e1356901-1-e1356901-21.

European Search Report of the Priority Application EP18215208.2, filed on Dec. 21, 2018, 44 Pages.

Supplemental Information of Natividad et al., 2020, 1 Page.

European Office Action for Appl No. 19813904.0-1105 dated Nov. 28, 2025, 46 pages.

* cited by examiner

NUTRITIONAL COMPOSITION COMPRISING A COMBINATION OF HUMAN MILK OLIGOSACCHARIDES TO IMPROVE THE GASTROINTESTINAL BARRIER

CROSS REFERENCE TO RELATED APPLICATIONS

The present application is a National Stage of International Application No. PCT/EP2019/084604, filed on Dec. 11, 2019, which claims priority to European Patent Application No. 18215208.2, filed on Dec. 21, 2018, the entire contents of which are being incorporated herein by reference.

TECHNICAL FIELD OF THE INVENTION

The present invention relates to nutritional compositions comprising 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) for use in improving gastrointestinal barrier. In particular, the present invention relates to improving the gastrointestinal barrier in an infant, a young child or children aged above 3 years to 8 years.

BACKGROUND OF THE INVENTION

Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients. In such cases, it would be even more preferred to provide means to improve gastrointestinal barrier in infants and young children through nutritional intervention, such as through complete nutrition or nutritional supplements.

During the postnatal development, the newborn intestine experiences a process of maturation that ends by the establishment of a functional barrier to macromolecules and pathogenic bacteria. This phenomenon is called gut closure and appears to be affected by the diet. Hence, different studies with infants (JPGN, 1995, 21:383-6) and animal models (Pediatr Res, 1990, 28:31-7) show that the maturation of the barrier is faster in breast-fed than in formula-fed newborns. This could explain the higher prevalence of allergy, inflammation and infection in infants fed formula than in those fed with mother milk.

Some specific populations of infants and young children are particularly in need of compositions able to provide health benefits such as improving gut barrier function. Such infants and young children are for example preterm infants, low birth weight infant, and/or growth-retarded infants or young children. Indeed the gut barrier is more permeable and more susceptible to injury and its structure and function are less mature in such infants than in a healthy term infant. This in turn may lead to other problems such as infection, inflammation or allergy. For such infants it is particularly advantageous to complement pharmacological management with nutritional compositions capable of improving gut barrier function.

The effect of nutritional ingredients, such as human milk oligosaccharides to improve gastrointestinal barrier has previously been investigated.

Diverse human milk oligosaccharides have been described as favourable to the gastrointestinal barrier in WO2013/032674 (gastrointestinal barrier function), WO2017/144062 (maintain or repair gastrointestinal barrier permeability via microbiota), WO2017/71716 (treat impaired mucosal barrier), WO2017/046711 (treat impaired mucosal barrier), WO2016/91265 (decrease gut permeability), WO2016/66174 (maintain mucosal integrity).

However, an improved nutritional composition would be advantageous, and in particular a more efficient and/or reliable nutritional composition for preterm infants would be advantageous.

It would be useful to further optimize the effect of nutritional compositions on gastrointestinal barrier in all infants and children.

There is clearly a need for developing suitable methods to improve gastrointestinal barrier in infants and young children.

There is also a need to deliver such health benefits in a manner that is particularly suitable for the young subjects (infants and young children), that does not involve a classical pharmaceutical intervention, as these infants or young children are particularly fragile.

There is a need to deliver such health benefits in these infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

Thus, there is clearly a need to develop alternative methods than the classical pharmaceutical intervention such as the use of pharmaceuticals, at least because of the associated risk of side effects.

SUMMARY OF THE INVENTION

The present invention relates to nutritional compositions comprising 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) for use in improving the gastrointestinal barrier. The effect is evidenced by the results of the in-vitro study on intestinal epithelium cell model. As disclosed in the example section, it has been found that a mix of 2'FL, DiFL, LNT, LNnT, 3'SL and 6'SL is particularly effective in improving the gastrointestinal barrier.

Thus, an object of the present invention relates to nutritional compositions, which improve the gastrointestinal barrier, such as improve barrier maturation, improve barrier protection, improve barrier structure, improve barrier function, and/or improve barrier repair. Such aspects of gastrointestinal barrier are all interrelated. Proper gastrointestinal maturation leads to proper gastrointestinal structure and function, which is in turn maintained by proper barrier protection and restored by proper barrier repair. Thus, any of these aspects, considered together or individually, contribute to sustained reduction of disease susceptibility.

Thus, one aspect of the invention relates to a nutritional composition comprising 2'FL, DiFL, LNT, LNnT, 3'SL and 6'SL for use in improving the gastrointestinal barrier in an infant (child under the age of 12 month) or a young child (between 1 year and less than 3 years); or a nutritional composition in the form of a growing-up milk comprising 2'FL, DiFL, LNT, LNnT, 3'SL and 6'SL for use in improving the gastrointestinal barrier in a child (aged from 3 years to less than 8 years).

In a preferred embodiment of the invention said improvement to the gastrointestinal barrier is improved barrier protection, improved barrier structure and improved barrier function, preferably improved barrier protection and/or improved barrier repair.

Figure 1:
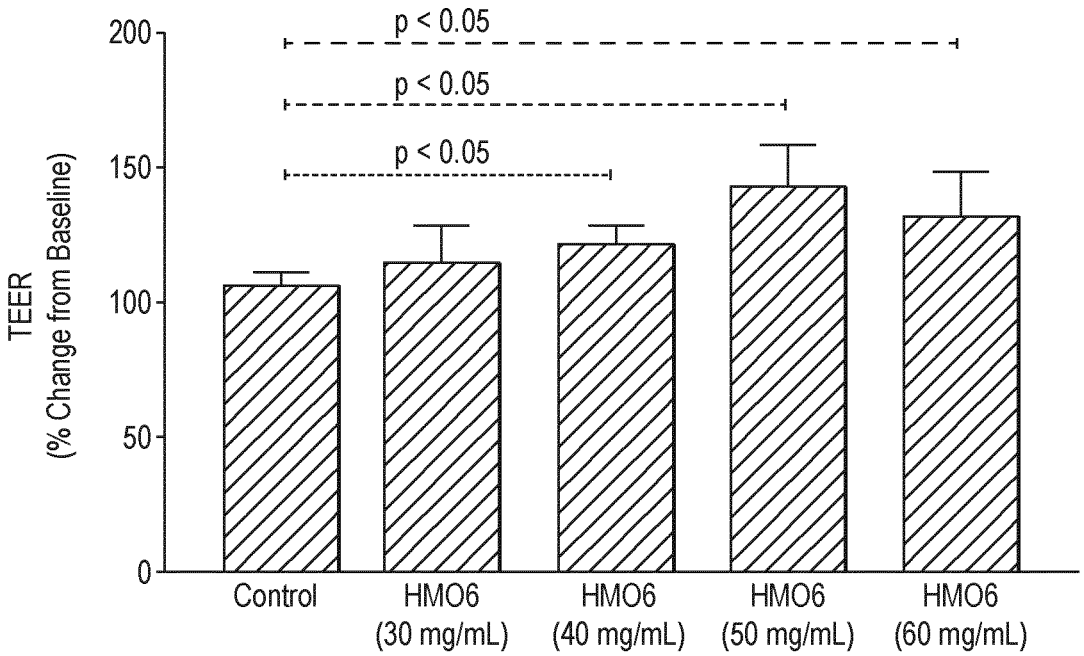
FIG. 1 shows Efficacy of HMO6 to provide prophylactic epithelial barrier protection. Co-cultures are treated with HMOs and permeability to ions is measured before induction of cytokine-mediated inflammation. Permeability to ions is calculated by analyzing the evolution of transepithelial electrical resistance (TEER) over time relative to baseline (time 0, before addition of HMO6) prior to inflammatory challenge. Error bars represent SD.

The present invention will now be described in more detail in the following.

DETAILED DESCRIPTION OF THE INVENTION

Definitions

Prior to discussing the present invention in further details, the following terms and conventions will first be defined:

The term "infant" means a child under the age of 12 months (<12 month). The expression "young child" means a child aged between one and less than three years (≥1 year to <3 years), also called toddler. The expression "child" means a child between three and less than eight years of age ((≥3 year to <8 years).

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 37 weeks of gestation.

An "infant having a low birth weight" means a new born having a body weight below 2500 g (5.5 pounds) either because of preterm birth or restricted fetal growth. It therefore encompasses:

infant or young child who has/had a body weight from 1500 to 2500 g at birth (usually called "low birth weight" or LBW)

infant or young child who has/had a body weight from 1000 to 1500 g at birth (called "very low birth weight" or VLBW)

infant or young child who has/had a body weight under 1000 g at birth (called "extremely low birth weight" or ELBW).

An "infant born small for gestational age (SGA)" means a baby with birth weights below the 10th percentile for babies of the same gestational age.

The expression "nutritional composition" means a composition which nourishes a subject. This nutritional composition is usually to be taken orally, and it usually includes a lipid or fat source and a protein source.

In a particular embodiment, the composition of the present invention is a hypoallergenic nutritional composition. The expression "hypoallergenic nutritional composition" means a nutritional composition which is unlikely to cause allergic reactions.

In a particular embodiment, the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2 (c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-based drink generally with added vitamins and minerals, that is intended for young children or children.

The term "fortifier" refers to liquid or solid nutritional compositions suitable for fortifying or mixing with human milk, infant formula, growing-up milk or human breast milk fortified with other nutrients. Accordingly, the fortifier of the present invention can be administered after dissolution in human breast milk, in infant formula, in growing-up milk or in human breast milk fortified with other nutrients or otherwise it can be administered as a stand-alone composition. When administered as a stand-alone composition, the milk fortifier of the present invention can be also identified as being a "supplement". In one embodiment, the milk fortifier of the present invention is a supplement.

The expression "weaning period" means the period during which the mother's milk is substituted by other food in the diet of an infant or young child.

The expressions "days/weeks/months/years of life" and "days/weeks/months/years of birth" can be used interchangeably.

The expression "improved gastrointestinal barrier", may encompass one or several of the following:

Improved barrier repair, such as (but not limited to) recovery of the integrity of the gastrointestinal barrier, such as repair of a disrupted barrier, reduction of permeability upon inflammatory challenge of the gastrointestinal mucosa, and mucosal repair.

Improved barrier maturation, such as (but not limited to) maturation and/or development of the barrier of an infant, preferably of a preterm infant.

Improved barrier structure, such as (but not limited to) strengthening of the gastrointestinal barrier, integrity of the gastrointestinal barrier, tight junction structure, and intestinal epithelial lining integrity.

Improved barrier function, such as improvement of gastrointestinal barrier resistance, reduction of gastrointestinal barrier permeability, such as reduction of pathogens to migrate out of the gut through the intestinal barrier, such as reduction of commensal bacteria or bacterial components to migrate out of the gut through the intestinal barrier, reduction of allergens to migrate out of the gut through the intestinal barrier, reduction of toxic compounds to migrate out of the gut through the intestinal barrier and reduction of disease susceptibility.

Improved barrier protection, such as (but not limited to) prevention of barrier dysfunction, prevention of barrier leakiness, protection of tight junction structure, protection of the intestinal epithelial lining integrity.

In a preferred embodiment, improving gastrointestinal barrier relates to maturation of the gastrointestinal barrier.

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" or "HMO's" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk-over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I fucosyllacto-N-hexaose, fucosyl-lacto-N-neohexaose, difucosyllacto-N-hexaose I difucosyl-lacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and without to be bound by theory, this is believed to therefore reduce the risk of infections/inflammations, and particularly the risk of LRT/ear infections and/or inflammations. In addition, the fucosylated oligosaccharides are thought to boost growth and metabolic activity of specific commensal microbes reducing inflammatory response and creating an environment unfavourable for pathogens thus leading to colonization resistance.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the LRT and/or ear infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) and any combinations thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or a growing-up milk or an infant cereal product or a fortifier or a supplement or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. *"Probiotics: how should they be defined"* Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

Nutritional Composition

As also outlined above. The present invention relates to nutritional compositions comprising 2'FL, DiFL, LNT, LNnT, 3'SL and 6'SL for use in improving the gastrointestinal barrier. As disclosed in the example section, it has been found that 2'FL, DiFL, LNT, LNnT, 3'SL and 6'SL is particularly effective in improving the gastrointestinal barrier. Thus an aspect of the invention relates to a nutritional composition comprising 2'FL, DiFL, LNT, LNnT, 3'SL and 6'SL for use in improving the gastrointestinal barrier in an infant (child under the age of 12 month) or a young child (between 1 year and less than 3 years);

or a nutritional composition in the form of a growing-up milk comprising 2'FL, DiFL, LNT, LNnT, 3'SL and 6'SL for use in improving the gastrointestinal barrier in a child (aged from 3 years to less than 8 years).

In an embodiment, said improvement to the gastrointestinal barrier is improved barrier maturation, improved barrier structure, improved barrier function improved barrier protection and/or improved barrier repair.

In another embodiment, said improvement to the gastrointestinal barrier is improved barrier function, improved barrier structure, and/or improved barrier protection.

In yet an embodiment, said improvement to the gastrointestinal barrier is improved barrier protection.

In yet another embodiment, said use is for improving the prevention of barrier dysfunction, the prevention of barrier leakiness, the protection of tight junction structure and the protection of the intestinal epithelial lining integrity. In a further embodiment, said prevention of barrier leakiness is prevention of pathogens, commensal bacteria, bacterial products, allergens and/or toxic compounds to migrate from the gut into the body through the intestinal barrier. As outlined in the examples, a mix of 2'FL, DiFL, LNT, LNnT, 3'SL and 6'SL has been found to improve in particular gastrointestinal barrier protection and gastrointestinal barrier structure.

The gastrointestinal barrier protection and structure result in improved gastrointestinal barrier function, as a gastrointestinal barrier missing proper structure and protection would lose its optimal function, namely upon inflammatory challenges.

Thus in an embodiment said use for improving gastrointestinal barrier protection is more particularly for improving the strength of the gastrointestinal barrier, integrity of the gastrointestinal barrier, tight junction structure, and intestinal epithelial lining integrity.

In a further preferred embodiment, said use is for improving the gastrointestinal barrier resistance and for reducing gastrointestinal barrier permeability. Preferably said use is for reducing pathogens to migrate out of the gut through the intestinal barrier, such as reduction of commensal bacteria to migrate out of the gut through the intestinal barrier, reduction of allergens to migrate out of the gut through the intestinal barrier, reduction of toxic compounds to migrate out of the gut through the intestinal barrier, and reduction of disease susceptibility.

In another embodiment, said use for improving gastrointestinal barrier structure is for improving the strength of the gastrointestinal barrier, improving the integrity of the gastrointestinal barrier, improving the tight junction structure, and improving intestinal epithelial lining integrity.

The above outlined effects/benefits are preferably obtained in the small intestine.

In yet an embodiment, the nutritional composition is formulated for administration to an infant. In another embodiment, said infant is selected from the group consisting of premature, small for gestational age and low birth weight babies, preferably the infant is premature. The nutritional compositions according to the invention are considered particularly useful for these types of infants, since the described benefits are more important for these infants than for "normal" infants, because the barrier is less mature and more permeable than in the healthy term infant.

In one embodiment, the nutritional composition comprises 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) in an amount of at least 0.3 g/L, for example at least 0.4 g/L, for example 0.5 g/L. In one embodiment, the nutritional composition comprises 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) in an amount of at least 0.3 g/L, for example at least 0.4 g/L, for example 0.5 g/L of the reconstituted product if the nutritional composition has to be reconstituted in water or any other liquid before consumption.

In one embodiment, the nutritional composition comprises 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) in an amount of at least 1.5 g/L, for example at least 2.0 g/L, for example 2.5 g/L. In one embodiment, the nutritional composition comprises 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) in an amount of at least 1.5 g/L, for example at least 2.0 g/L, for example 2.5 g/L of the reconstituted product if the nutritional composition has to be reconstituted in water or any other liquid before consumption.

In some embodiments, 2'FL may be in an amount of 0.005-5 g/L of the composition, such as 0.01-3 g/L or 0.02-2 g/L or 0.1-2.5 g/L or 0.15-2 g/L or 0.25-1.9 g/L or 0.75-1.65 g/L of the composition. In a particular embodiment, 2'FL is in an amount of 1 g/L of the composition. In another particular embodiment, 2'FL is in an amount of 0.25 or 0.26 g/L of the composition. In one embodiment 2'FL is in an amount of more than 0.1 g/L and optionally less than 1 g/L or more than 0.2 and less than 0.8 g/L. In one embodiment 2'FL is present in an amount of at least 0.1 g/L, at least 0.25, at least 0.26, at least 0.5, at least 0.7, at least 0.8, at least 1, at least 1.25, at least 1.5 at least 1.5 or at least 2 g/L.

2'FL can be present in the nutritional composition in a total amount of 0.004-3.8 g/100 g of composition on a dry weight basis. 2'FL may be in an amount of 0.008-2.3 g/100 g of the composition, such as 0.015-1.5 g/100 g, or 0.08-1.9 g/100 g or 0.12-1.5 g/100 g or 0.15-1.5 g/100 g or 0.19-1.5 g/100 g of the composition. In a particular embodiment, 2'FL is in an amount of 0.075 or 0.78 g/100 g of the composition. In another particular embodiment, 2'FL is in an amount of 0.2 g/100 g of the composition. In a particular embodiment, 2'FL is in an amount of at least 0.01 g/100 g, at least 0.02 g/100 g, at least 0.05 g/100 g, at least 0.1 g/100 g, at least 0.2 g/100 g, at least 0.25 g/100 g, at least 0.4 g/100 g, at least 0.5 g/100 g, at least 0.75 g/100 g, at least 0.9 g/100 g, at least 1 g/100 g, at least 1.5 g/100 g, at least 2 g/100 g or at least 3 g/100 g of the composition.

In a particular embodiment, 2'FL is provided in the nutritional composition of the present invention in such an amount that normal consumption of the nutritional composition would provide to the infant or young child, respectively the child, consuming it a total daily dose of 0.003-6.5 g, preferably 0.006-3.9 g, for example 0.012-2.6 g per day. It is believed that a minimal amount of 2'FL is necessary to have the desired effect in a measurable way.

For preterm, low birth weight and small for gestational age infants, the daily dose of 2'FL is preferably of 0.05 to 1 g/kg of body weight per day, preferably 0.06-0.9 g or 0.07-0.8 g or 0.08-0.7 g or 0.09-0.6 g or 0.1-0.5 g or 0.2-0.4 g/, most preferably 0.34 g per kg of body weight and per day.

In some embodiments, DiFL may be in an amount of 0.0005-0.5 g/L of the composition, such as 0.001-0.3 g/L or 0.002-0.2 g/L or 0.01-0.25 g/L or 0.015-0.2 g/L or 0.025-0.19 g/L or 0.075-0.165 g/L of the composition. In a particular embodiment, DiFL is in an amount of 0.1 g/L of the composition. In another particular embodiment, DiFL is in an amount of 0.025 or 0.026 g/L of the composition. In one embodiment DiFL is in an amount of more than 0.01 g/L and optionally less than 0.1 g/L or more than 0.02 and less than 0.08 g/L. In one embodiment DiFL is present in an amount of at least 0.01 g/L, at least 0.025, at least 0.026, at least 0.05, at least 0.07, at least 0.08, at least 0.1, at least 0.125, at least 0.15 at least 0.15 or at least 0.2 g/L.

DiFL can be present in the nutritional composition in a total amount of 0.0004-0.38 g/100 g of composition on a dry weight basis. DiFL may be in an amount of 0.0008-0.23 g/100 g of the composition, such as 0.0015-0.15 g/100 g, or 0.008-0.19 g/100 g or 0.012-0.15 g/100 g or 0.015-0.15 g/100 g or 0.019-0.15 g/100 g of the composition. In a particular embodiment, 2DiFL is in an amount of 0.0075 or 0.078 g/100 g of the composition. In another particular embodiment, DiFL is in an amount of 0.02 g/100 g of the composition. In a particular embodiment, DiFL is in an amount of at least 0.001 g/100 g, at least 0.002 g/100 g, at least 0.005 g/100 g, at least 0.01 g/100 g, at least 0.02 g/100 g, at least 0.025 g/100 g, at least 0.04 g/100 g, at least 0.05 g/100 g, at least 0.075 g/100 g, at least 0.09 g/100 g, at least 0.1 g/100 g, at least 0.15 g/100 g, at least 0.2 g/100 g or at least 0.3 g/100 g of the composition.

In some embodiments, LNnT may be in an amount of 0.0005-0.5 g/L of the composition, such as 0.001-0.3 g/L or 0.002-0.2 g/L or 0.01-0.25 g/L or 0.015-0.2 g/L or 0.025-0.19 g/L or 0.075-0.165 g/L of the composition. In a particular embodiment, LNnT is in an amount of 0.1 g/L of the composition. In another particular embodiment, LNnT is in an amount of 0.025 or 0.026 g/L of the composition. In one embodiment LNnT is in an amount of more than 0.01 g/L and optionally less than 0.1 g/L or more than 0.02 and less than 0.08 g/L. In one embodiment LNnT is present in an amount of at least 0.01 g/L, at least 0.025, at least 0.026, at least 0.05, at least 0.07, at least 0.08, at least 0.1, at least 0.125, at least 0.15 at least 0.15 or at least 0.2 g/L.

LNnT can be present in the nutritional composition in a total amount of 0.0004-0.38 g/100 g of composition on a dry weight basis. LNnT may be in an amount of 0.0008-0.23 g/100 g of the composition, such as 0.0015-0.15 g/100 g, or 0.008-0.19 g/100 g or 0.012-0.15 g/100 g or 0.015-0.15 g/100 g or 0.019-0.15 g/100 g of the composition. In a particular embodiment, LNnT is in an amount of 0.0075 or 0.078 g/100 g of the composition. In another particular embodiment, LNnT is in an amount of 0.02 g/100 g of the composition. In a particular embodiment, LNnT is in an amount of at least 0.001 g/100 g, at least 0.002 g/100 g, at least 0.005 g/100 g, at least 0.01 g/100 g, at least 0.02 g/100 g, at least 0.025 g/100 g, at least 0.04 g/100 g, at least 0.05 g/100 g, at least 0.075 g/100 g, at least 0.09 g/100 g, at least 0.1 g/100 g, at least 0.15 g/100 g, at least 0.2 g/100 g or at least 0.3 g/100 g of the composition. In some embodiments, 3SL may be in an amount of 0.0005-0.5 g/L of the composition, such as 0.001-0.3 g/L or 0.002-0.2 g/L or 0.01-0.25 g/L or 0.015-0.2 g/L or 0.025-0.19 g/L or 0.075-0.165 g/L of the composition. In a particular embodiment, 3SL is in an amount of 0.1 g/L of the composition. In another particular embodiment, 3SL is in an amount of 0.025 or 0.026 g/L of the composition. In one embodiment 3SL is in an amount of more than 0.01 g/L and optionally less than 0.1 g/L or more than 0.02 and less than 0.08 g/L. In one embodiment 3SL is present in an amount of at least 0.01 g/L, at least 0.025, at least 0.026, at least 0.05, at least 0.07, at least 0.08, at least 0.1, at least 0.125, at least 0.15 at least 0.15 or at least 0.2 g/L.

3SL can be present in the nutritional composition in a total amount of 0.0004-0.38 g/100 g of composition on a dry weight basis. 3SL may be in an amount of 0.0008-0.23 g/100 g of the composition, such as 0.0015-0.15 g/100 g, or 0.008-0.19 g/100 g or 0.012-0.15 g/100 g or 0.015-0.15 g/100 g or 0.019-0.15 g/100 g of the composition. In a particular embodiment, 3SL is in an amount of 0.0075 or 0.078 g/100 g of the composition. In another particular embodiment, 3SL is in an amount of 0.02 g/100 g of the composition. In a particular embodiment, 3SL is in an amount of at least 0.001 g/100 g, at least 0.002 g/100 g, at least 0.005 g/100 g, at least 0.01 g/100 g, at least 0.02 g/100 g, at least 0.025 g/100 g, at least 0.04 g/100 g, at least 0.05 g/100 g, at least 0.075 g/100 g, at least 0.09 g/100 g, at least 0.1 g/100 g, at least 0.15 g/100 g, at least 0.2 g/100 g or at least 0.3 g/100 g of the composition.

LNT is present in the nutritional in an amount of 0.005-3 g/L of the composition. In some embodiments, LNT may be in an amount of 0.01-1.5 g/L of the composition, such as 0.04-1.2 g/L or 0.05-1 g/L or 0.09-0.8 g/L of the composition. In a particular embodiment, LNT is in an amount of 0.5 g/L of the composition. In another particular embodiment, LNT is in an amount of 0.1 g/L of the composition.

LNT can be present in the nutritional composition an amount of 0.004-2.3 g/100 g of composition on a dry weight basis, LNT may be present in an amount of 0.008-1.2 g/100 g of composition, such as 0.03-0.9 g/100 g or 0.04-0.8 g/100 g or 0.07-0.6 g/100 g of the composition. In a particular embodiment, LNT is present in an amount of 0.38 g/100 g of the composition. In another particular embodiment, LNT is present in an amount of 0.08 g/100 g of the composition.

In another embodiment of the invention the nutritional composition may comprise from 0.005-5 g/L of 6'SL, or from 0.008-2.5 g/L, or from 0.01-1 g/L, or from 0.03-0.7 g/L, for example 0.04 or 0.5 g/L.

The nutritional composition the invention can contain 0.004-3.8 g of 6'SL per 100 g of composition on a dry weight basis, e.g. 0.006-1.9 g or 0.008-0.8 g or 0.023-0.5 g or 0.031-0.4 of 6'SL per 100 g of composition on a dry weight basis, for example 0.18 g or 0.04 g per 100 g of composition on a dry weight basis.

In a particular embodiment, the 6'SL and the LNT comprised in the nutritional composition or the growing-up milk according to the invention are typically present in a ratio 6'SL:LNT of from 3:1 to 1:3, such as 2:1 to 1:2 or 2:1 to 1:1. In a particularly advantageous embodiment, this ratio is 2:1 or around 2.1 or this ratio is 1:1 or around 1:1.

In one additional embodiment, the nutritional composition of the invention comprises 2'FL in an amount of 0.005-5 g/L of the composition, such as 0.01-3 g/L or 0.02-2 g/L or 0.1-2.5 g/L or 0.15-2 g/L or 0.25-1.9 g/L or 0.75-1.65 g/L of the composition; DiFL in an amount of 0.0005-0.5 g/L of the composition, such as 0.001-0.3 g/L or 0.002-0.2 g/L or 0.01-0.25 g/L or 0.015-0.2 g/L or 0.025-0.19 g/L or 0.075-0.165 g/L of the composition;

LNnT in an amount of 0.0005-0.5 g/L of the composition, such as 0.001-0.3 g/L or 0.002-0.2 g/L or 0.01-0.25 g/L or 0.015-0.2 g/L or 0.025-0.19 g/L or 0.075-0.165 g/L of the composition; 3SL in an amount of 0.0005-0.5 g/L of the composition, such as 0.001-0.3 g/L or 0.002-0.2 g/L or 0.01-0.25 g/L or 0.015-0.2 g/L or 0.025-0.19 g/L or 0.075-0.165 g/L of the composition; LNT in an amount of 0.005-3 g/L of the composition, for example in an amount of 0.01-1.5 g/L of the composition, such as 0.04-1.2 g/L or 0.05-1 g/L or 0.09-0.8 g/L of the composition; and 6SL in an amount of 0.005-5 g/L, or from 0.008-2.5 g/L, or from 0.01-1 g/L, or from 0.03-0.7 g/L, for example 0.04 or 0.5 g/L.

In an embodiment, the composition further comprises one or more additional HMO or one or more precursor thereof.

In one embodiment, the composition of the invention comprises at least one N-acetylated oligosaccharide in addition to LNT and LNnT. In one embodiment the N-acetylated oligosaccharide is para-lacto-N-neohexaose (para-LNnH), disialyllacto-N-tetraose (DSLNT) or any combination thereof.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

In a particularly advantageous embodiment of the present invention, the N-acetylated oligosaccharide(s) are present in the nutritional composition in some particular amounts. The term "amount" refers to the total amount of each of these two components in the nutritional composition unless otherwise specified. It therefore does not refer to an individual amount except when there is a single type of these components (in that case both the total and individual amounts equal). The same applies for all compounds/ingredients of the invention. By way of illustrative example, if there is only one (i.e. only one type of) N-acetylated oligosaccharide in the composition (e.g. LNnT), its individual amount (and therefore the total amount of N-acetylated oligosaccharides) will be in the range 0.75-1.65 g/L. If there are several (i.e. several types of) N-acetylated oligosaccharides, their individual amount will be lower (e.g. if there are 2 different types of N-acetylated oligosaccharide, e.g. LNnT+LNT, there may be for example each in an individual amount of 0.5 g/L) but the total amount of N-acetylated oligosaccharides will be in the range 0.75-1.65 g/L.

In a particular embodiment, the N-acetylated oligosaccharide is provided in the nutritional composition of the present invention in such an amount that normal consumption of the nutritional composition would provide to the infant or young child, respectively the child, consuming it a total daily dose of 0.003-3.9 g, preferably 0.006-3.25 g or 0.03-1.95 g or 0.03-1.3 g or 0.03-1 g, for example 0.05-1 g per day.

For preterm, low birth weight and small for gestational age infants, the daily dose is preferably of 0.005 to 0.1 g/kg of body weight per day, preferably 0.006-0.09 g or 0.007-0.08 g or 0.008-0.07 g or 0.009-0.06 g or 0.01-0.05 g or 0.02-0.04 g/, most preferably 0.034 g per kg of body weight and per day.

When both 2'FL and N-acetylated oligosaccharides are present, 2'FL and the N-acetylated oligosaccharide(s) comprised in the nutritional composition according to the invention are typically present in an N-acetylated oligosaccharide(s): 2'FL ratio of from 1:20 to 2:1, preferably 1:15 to 1:1, most preferably of 1:10 to 1:2. In a particularly advantageous embodiment, this ratio is (or is around) 1:2, 1:5, or 1:10.

The sialylated oligosaccharide(s) 3'SL and 6'SL may be isolated by chromatographic or filtration technology from a natural source such as animal milks. Alternatively, they may be produced by biotechnological means using specific sialyl-transferases or sialyldases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In another preferred embodiment of the invention the nutritional composition may comprise from 0.005-5 g/L of sialylated oligosaccharides, or 0.008-2.5 g/L, or 0.01-1 g/L, or 0.02-0.7 g/L, for example 0.03-0.5 g/L.

The nutritional composition according to the invention can contain 0.004-3.8 g of sialylated oligosaccharides per 100 g of composition on a dry weight basis, e.g. 0.006-1.9 g or 0.008-0.8 g or 0.015-0.5 g, for example 0.023-0.4 of sialylated oligosaccharides per 100 g of composition on a dry weight basis.

In some particular embodiments of the present invention, the nutritional composition comprises sialylated oligosaccharide(s) in an amount of below 0.1 g/100 g of composition on a dry weight basis.

In a particular embodiment, the sialylated oligosaccharide is provided in the nutritional composition of the present invention in such an amount that normal consumption of the nutritional composition or would provide to the infant or young child, respectively the child, consuming it a total daily dose of 0.003-6.5 g, preferably 0.005-3.3 g or 0.006-1.3 g or 0.01-0.9 g, for example 0.018-0.65 g per day.

The nutritional composition according to the present invention may optionally also comprise at least one precursor of oligosaccharide. There can be one or several precursor(s) of oligosaccharide. For example the precursor of human milk oligosaccharide is sialic acid, fucose or a mixture thereof. In some particular embodiments the composition comprises sialic acid.

In particular examples the nutritional composition comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide. The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition of the present invention may comprises at least one further fucosylated oligosaccharide in addition to 2'FL and DiFL. There can be one or several types of fucosylated oligosaccharide(s). The fucosylated oligosaccharide(s) can indeed be selected from the list comprising 3'fucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the further fucosylated oligosaccharide comprises a 2'-fucosyl-epitope. It can be for example selected from the list comprising lacto-N-fucopentaose, lacto-N-fucohexaose, lacto-N-difucohexaose, fucosyllacto-N-hexaose, fucosyllacto-N-neohexaose, difucosyl-lacto-N-hexaose difuco-lacto-N-neohexaose, difucosyllacto-N-neohexaose, fucosyl-para-Lacto-N-hexaose and any combination thereof, preferably difucosyllactose.

In a particular embodiment, there is no other type of fucosylated oligosaccharide than 2'-fucosyllactose and difucosyllactose, i.e. the nutritional composition of the invention comprises only 2'-fucosyllactose and di-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

In another specific embodiment, the nutritional composition of the present invention comprises an oligosaccharide mixture that consists of 2'FL, 6'SL, LNT, DIFL, LNnT and 3'SL. In other words, it does not contain any further human milk oligosaccharides.

The nutritional composition or the growing-up milk according to the present invention may also comprise other types of oligosaccharide(s) (i.e. other than human milk oligosaccharides mentioned above) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose and any combination thereof. They may be in an amount between 0 and 10% by weight of composition. In a particular embodiment, the nutritional composition or the growing-up milk can also contain at least one BMO (bovine milk oligosaccharide).

Suitable commercial products that can be used to prepare the nutritional compositions or the growing-up milk according to the invention include combinations of FOS with inulin such as the product sold by BENEO under the trademark Orafti, or polydextrose sold by Tate & Lyle under the trademark STA-LITE®.

The nutritional composition or the growing-up milk according to the present invention may optionally also comprise at least one precursor of oligosaccharide.

There can be one or several precursor(s) of oligosaccharide. For example the precursor of human milk oligosaccharide is sialic acid, fucose or a mixture thereof. In some particular embodiments the composition comprises sialic acid.

In particular examples the nutritional composition or the growing-up milk comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide. The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition or the growing-up milk of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus johnsonii* CNCM I-1225, *Streptococcus salivarius* DSM 13084 sold by BLIS Technologies Limited of New Zealand under the designation KI2, *Bifidobacterium*

*lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition or the growing-up milk according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments. Probiotic components and metabolites can also be added.

In one embodiment, the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

In some particular embodiments, the composition of the invention is an infant formula, a fortifier or a supplement that may be intended for the first 4, 6 or 12 months of age. In a preferred embodiment the nutritional composition of the invention is an infant formula. It is indeed believed that the nutritional intervention of the invention may be most effective when enacted at an early stage of life (for example the first 1, 4, 6, 12 months of age).

The nutritional composition according to the invention can be for example an infant formula, a starter infant formula, a follow-on or follow-up formula, a growing-up milk, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses. In such cases it is particularly useful to define the amount of 2'FL and optionally other oligosaccharides in terms or daily dose to be administered to the infant or young child, such as described above.

The nutritional composition of the present invention can be in solid (e.g. powder), liquid or gelatinous form.

In a specific embodiment the nutritional composition is a supplement in powder form and provided in a sachet, in the form of tablets, capsules, pastilles or a liquid, such as a liquid to be dispensed as drops in breast milk or in a nutritional composition or directly in the mouth of an infant or a young child.

In another embodiment, the supplement may further contain a carrier, protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. When the supplement is in powder form, it may comprise a carrier. It is however preferred that the supplement is devoid of a carrier. When the supplement is in the form of a syrup, the HMOs are preferably dissolved or suspended in water acidified with citrate.

Further, the supplement may contain vitamins, minerals trace elements and other micronutrients in accordance with the recommendations of Government bodies such as the USRDA.

The nutritional composition of the present invention can be in solid (e.g. powder), liquid or gelatinous form. In a specific embodiment the nutritional composition is a supplement comprising 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL), wherein the supplement is in powder form and provided in a sachet, preferably a sachet with 1 to 10 g of the mixture of 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) per sachet, or in the form of a syrup, preferably a syrup with a total solid concentration of 5 to 75 g/100 mL (5 to 75% (w/v)). When the supplement is in powder form, it may comprise a carrier. It is however preferred that the supplement is devoid of a carrier. When the supplement is in the form of a syrup, the HMOs are preferably dissolved or suspended in water acidified with citrate.

The nutritional composition or the growing-up milk according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments, the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids. The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

The protein component can alternatively be replaced by a mixture or synthetic amino acid, for example for preterm or low birth weight infants.

In a particular embodiment the nutritional composition or the growing-up milk according to the invention is a hypoallergenic composition. In another particular embodiment the composition according to the invention is a hypoallergenic nutritional composition or growing-up milk.

The nutritional composition or the growing-up milk according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition or the growing-up milk according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, structured triglyceride oil, high oleic sunflower oil and high oleic safflower oil, medium-chain-triglyceride oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition or the growing-up milk of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition or the growing-up milk of the invention may contain emulsifiers and stabilisers such as soy, lecithin, citric acid esters of mono- and diglycerides, and the like.

The nutritional composition or the growing-up milk of the invention may also contain other substances which may have a beneficial effect such as lactoferrin, nucleotides, nucleosides, and the like.

The nutritional composition or the growing-up milk of the invention may also contain carotenoid(s). In some particular embodiments of the invention, the nutritional composition of the invention does not comprise any carotenoid.

The nutritional composition or the growing-up milk according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm, having a low birth weight and/or born small for gestational age (SGA). In a particular embodiment the nutritional composition of the invention is for use in preterm infants, infants having a low birth weight and/or infants born small for gestational age (SGA).

The nutritional composition of the present invention may also be used in an infant or a young child that was born by C-section or that was vaginally delivered.

In some embodiments the composition according to the invention can be for use before and/or during the weaning period.

The nutritional composition can be administered (or given or fed) at an age and for a period that depends on the needs.

The nutritional composition can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4, 6 or 12 months of birth of said infant. In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

All patent and non-patent references cited in the present application, are hereby incorporated by reference in their entirety.

The invention will now be described in further details in the following non-limiting examples.

EXAMPLES

Example 1

An example of the composition of a nutritional composition (e.g. an infant formula) according to the present invention is given in the below table 1. This composition is given by way of illustration only.

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 10.6 | 70.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |

-continued

| Nutrients | | per 100 kcal | per litre |
|---|---|---|---|
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides | 2FL (g) | 0.13 | 0.9 |
| (HMOs) | LNnT (g) | 0.0075 | 0.05 |
| | LNT (g) | 0.04 | 0.25 |
| | DFL (g) | 0.013 | 0.09 |
| | 3SL(g) | 0.014 | 0.1 |
| | 6SL (g) | 0.022 | 0.15 |

Table 1: an example of the composition of a nutritional composition (e.g. an infant formula) according to the present invention

Example 2

A Blend of 6 HMOs Conferred Resistance Against Inflammatory-Induced Epithelial Barrier Dysfunction Cell Lines The human colorectal adenocarcinoma cell line Caco-2 (HTB-37) was obtained from the American Type Culture Collection (ATCC, Manassas, USA) at passage 21 and used in experiments at passage 23 to 33. The human colon adenocarcinoma cell line HT29 (HTB-38; ATCC) previously adapted with methotrexate (MTX) was obtained from European Collection of Authenticated Cell Cultures (ECACC, Salisbury, UK) at passage 51 and used in experiments at passage 23 to 33. Both cell lines were separately maintained in 75-cm$^2$ tissue culture flasks (Fischer Scientific) in a humidified atmosphere of 37° C. and 10% CO2, 95% air/water saturated atmosphere.

Cell Culture Model.

Both Caco-2 and HT29-MTX cell lines were maintained in Dulbecco's Minimal Essential Media (DMEM; 11965092, Gibco) supplemented with 10% (v/v) heat-inactivated FBS (10270-106, Gibco) and 1% (v/v) Penicillin and Streptomycin solution (P4333, Sigma). Growth medium was replaced at a minimum of twice per week. Cell lines were subcultured weekly at preconfluent densities with 0.4% trypsin-EDTA (T3924, Sigma).

For the experimental studies, Caco-2 and HT29-MTX cells were stained with trypan blue (T8154, Sigma), counted, resuspended in complete growth medium at ratios 76:24 to simulate the large intestine, and seeded at a density of 6×10$^4$ cells per cm$^2$ in Transwell™ Polycarbonate semipermeable membrane of 0.4 µM pore size and 1.12 cm$^2$ surface area (3460, Corning. Confluency and integrity of the Caco-2:HT29-MTX culture was evaluated by measuring manually the transepithelial electrical resistance every week using Millicell™ ERS-2 Voltohmmeter. Cells were used for experiments 21-days post seeding.

HMO Treatments and Inflammation-Induced Epithelial Barrier Dysfunction Model.

HMOs, obtained from Glycom (Hørsholm, Denmark), were diluted in sterile water at a concentration of 250 mg/ml, and filtered using 0.2 µM pore size filter and kept at −20° C.

for maximum of 6 months. On the day of the treatment, cell growth medium were replaced by fresh medium with all supplements but without phenol red. Blends of 2'FL:3'SL:6'SL:LNnT:LNT:diFL at a proportion of 0.55:0.7:0.09:0.05:0.18:0.06 were further diluted in the growth medium and added in the apical compartment of the Transwell™ at varying final concentration 48 hours before challenging with TNF-α and IFN-γ cytokines in basolateral compartment for an additional 48 hours. Controls were non-HMO treated cells and cytokine unchallenged cells (Control −ve) and non-HMO treated cells but cytokine challenged cells (Control +ve).

Epithelial Permeability Assessment.

Permeability was assessed using two readouts: transepithelial electrical resistance (TEER) and translocation of FITC-labeled dextran (FD4; 4000 Da, Sigma) from apical to basolateral compartment of the Transwell™.

TEER was dynamically measured every 5-15 minutes by placing the Transwell™ seeded with Caco-2:HT29-MTX culture in the cellZscope machine (Nano Analytics) inside a humidified atmosphere of 37° C. and 10% CO2, 95% air/water saturated atmosphere for the whole duration of experiment. Growth medium and treatments were replenished every 48 hours. TEER was measured as 22 per cm$^2$ and percent changes in TEER were calculated relative to the baseline value (TEER measurement prior to any treatment).

FD4 translocation was measured by adding a filter-sterilized solution of FD4 in the apical compartment of Transwell™ at a final concentration of 1 mg/ml at the end of the inflammatory challenge. Basolateral samples were collected before and every 30 minutes for 2 hours after the apical addition of FD4. FD4 translocation was measured by interpolating the fluorescent intensity in the samples against a standard curve and expressed as ng/ml. FD4 translocation was normalized relative to both Control +ve and Control −ve cells. Control +ve represent minimum resistance to FD4 translocation while control −ve represent maximal resistance to FD4 translocation.

Results

Figure 2:
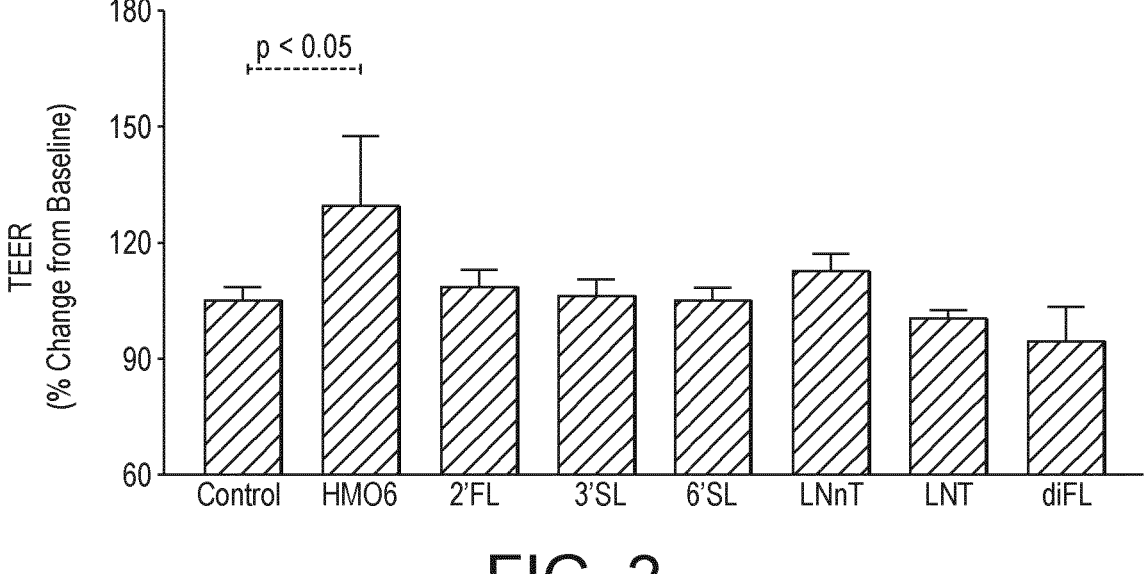
FIG. 2 Efficacy of HMO6 to provide prophylactic epithelial barrier protection. Co-cultures are treated with HMOs at equal concentration (60 mg/ml) and permeability to ions is measured before induction of cytokine-mediated inflammation. Permeability to ions is calculated by analyzing the evolution of transepithelial electrical resistance (TEER) over time relative to baseline (time 0, before addition of HMOs) prior to inflammatory challenge. Error bars represent SD.
Figure 3:
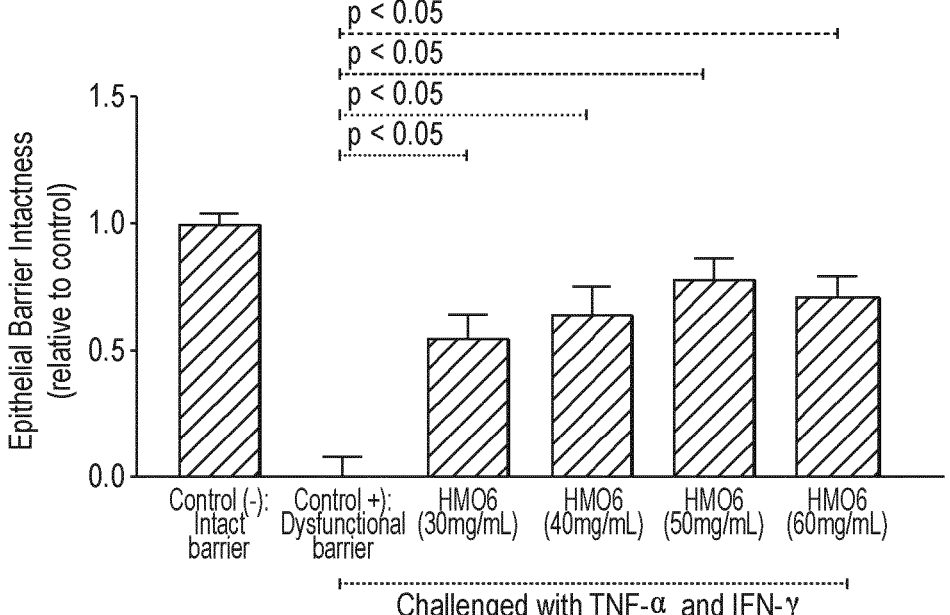
FIG. 3 shows Efficacy of HMO6 to reduce symptoms severity of inflammation-induced epithelial barrier dysfunction. Co-cultures are treated with HMO6 and then epithelial barrier dysfunction is induced by cytokine-mediated inflammation. All groups, in exception of control –ve (intact barrier), are inflammatory challenged. The graph represents translocation of FITC-labeled dextran (FD4) from apical to basolateral compartment after inflammatory challenge relative to controls. Error bars represent SD.

HMO6 increased TEER before the inflammatory challenge in a dose-dependent manner compared to either lactose or untreated controls (FIG. 1). Furthermore, HMO6 showed significant increase in TEER before inflammation compared to individual HMOs, suggesting the efficacy of a complex blend over individual HMOs (FIG. 2). After the inflammatory challenge, HMO6 significantly prevented the increased translocation of FD4 from apical to basolateral compartment, in a dose dependent manner, compared to lactose-treated and non-treated control cells (FIG. 3). Overall, this highlighted that HMO6 provides health benefits by prophylactically tightening the epithelial barrier and conferring resistance to inflammation mediated barrier dysfunction.

The invention claimed is:

1. A method for improving a gastrointestinal barrier in an infant (child under the age of 12 months), the method comprising administering a synthetic nutritional composition comprising 2'-Fucosyllactose (2'FL), Di-fucosyllactose (DiFL), Lacto-N-tetraose (LNT), Lacto-N-neotetraose (LNnT), 3'-Sialyllactose (3'SL) and 6'-Sialyllactose (6'SL) to the infant, wherein the improving the gastrointestinal barrier comprises improving barrier repair and wherein the infant is selected from the group consisting of a premature baby, a small for gestational age baby and a low birth weight baby.

2. The method according to claim 1, wherein the improving the gastrointestinal barrier further comprises improving barrier maturation, and/or improving barrier function.

3. The method according to claim 1, wherein the improving the gastrointestinal barrier further comprises improving barrier function.

4. The method according to claim 1, wherein the improving the gastrointestinal barrier further comprises improving barrier protection, and wherein the improving barrier protection comprises improving prevention of barrier dysfunction, improving prevention of barrier leakiness, improving protection of tight junction structure and improving protection of intestinal epithelial lining integrity.

5. The method according to claim 4, wherein the prevention of barrier leakiness comprises prevention of pathogens, allergens and/or toxic compounds to migrate from the gut into the body through the intestinal barrier.

6. The method according to claim 1, wherein the improving the gastrointestinal barrier further comprises improving barrier structure, and wherein the improving barrier structure comprises improving strength of the gastrointestinal barrier, improving integrity of the gastrointestinal barrier, improving tight junction structure, and improving intestinal epithelial lining integrity.

7. The method according to claim 1, wherein the synthetic nutritional composition comprises the 2'-Fucosyllactose (2'FL), the Di-fucosyllactose (DiFL), the Lacto-N-tetraose (LNT), the Lacto-N-neotetraose (LNnT), the 3'-Sialyllactose (3'SL) and the 6'-Sialyllactose (6'SL) in a total amount of at least 0.3 g/L of the synthetic nutritional composition.

8. The method according to claim 1, wherein the synthetic nutritional composition is selected from the group consisting of an infant formula, a starter infant formula, a follow-on or follow-up infant formula, a growing-up milk, a baby food, an infant cereal composition, a fortifier and a supplement.

9. The method according to claim 1, wherein the 2'FL, the DiFL, the LNT, the LNnT, the 3'SL and the 6'SL are the only human milk oligosaccharides in the synthetic nutritional composition.

10. The method according to claim 1, wherein the improving the gastrointestinal barrier further comprises improving barrier protection.

11. The method according to claim 1, wherein the 2'FL is 0.01-3 g/L of the synthetic nutritional composition, the DiFL is 0.001-0.3 g/L of the synthetic nutritional composition; the LNT is 0.01-1.5 g/L of the synthetic nutritional composition; the LNnT is 0.001-0.3 g/L of the synthetic nutritional composition; the 3'SL is 0.001-0.3 g/L of the synthetic nutritional composition; and the 6'SL is 0.008-2.5 g/L of the synthetic nutritional composition.

* * * * *